United States Patent [19]

Kaper

[11] Patent Number: 4,818,552

[45] Date of Patent: Apr. 4, 1989

[54] PROCESS FOR RECOVERING CAFFEINE ADSORBED TO ACTIVATED CARBON

[75] Inventor: Louris Kaper, Barneveld, Netherlands

[73] Assignee: Douwe Egberts Koninklijke Tabaksfabriek-Koffiebranderijen-Theehandel N.V., Utrecht, Netherlands

[21] Appl. No.: 82,341

[22] Filed: Aug. 6, 1987

[30] Foreign Application Priority Data

Aug. 6, 1986 [NL] Netherlands ............... 8602012

[51] Int. Cl.$^4$ ............ A23F 5/22; C07D 473/12
[52] U.S. Cl. .................... 426/422; 426/424; 426/427; 426/428; 544/274; 544/275
[58] Field of Search ................ 544/274–275; 426/422, 424, 427, 428

[56] References Cited

U.S. PATENT DOCUMENTS

| | | | |
|---|---|---|---|
| 4,298,736 | 11/1981 | Katz et al. | 544/274 |
| 4,443,601 | 4/1984 | Karmiol et al. | 544/274 |
| 4,481,223 | 11/1984 | Hinman et al. | 544/274 X |
| 4,506,072 | 3/1985 | Gehrig et al. | 544/274 |
| 4,513,136 | 4/1985 | Katz et al. | 544/274 X |
| 4,540,784 | 9/1985 | Vitzlium et al. | 544/274 |
| 4,548,827 | 10/1985 | Katz et al. | 544/274 X |
| 4,673,743 | 6/1987 | Wilkens | 544/275 |

*Primary Examiner*—Joseph Golian
*Attorney, Agent, or Firm*—Cushman, Darby & Cushman

[57] ABSTRACT

This invention relates to a process for recovering caffeine from laden activated carbon by treating the laden activated carbon with an organic acid. In order to achieve good extraction efficiencies, on the one hand, and to avoid problems with the flash point, such as with acetic acid, on the other hand, the process according to the invention is characterized by treating the activated carbon with a mixture comprising at least 65% by weight of acetic acid and at least 2% by weight of citric acid.

8 Claims, 1 Drawing Sheet

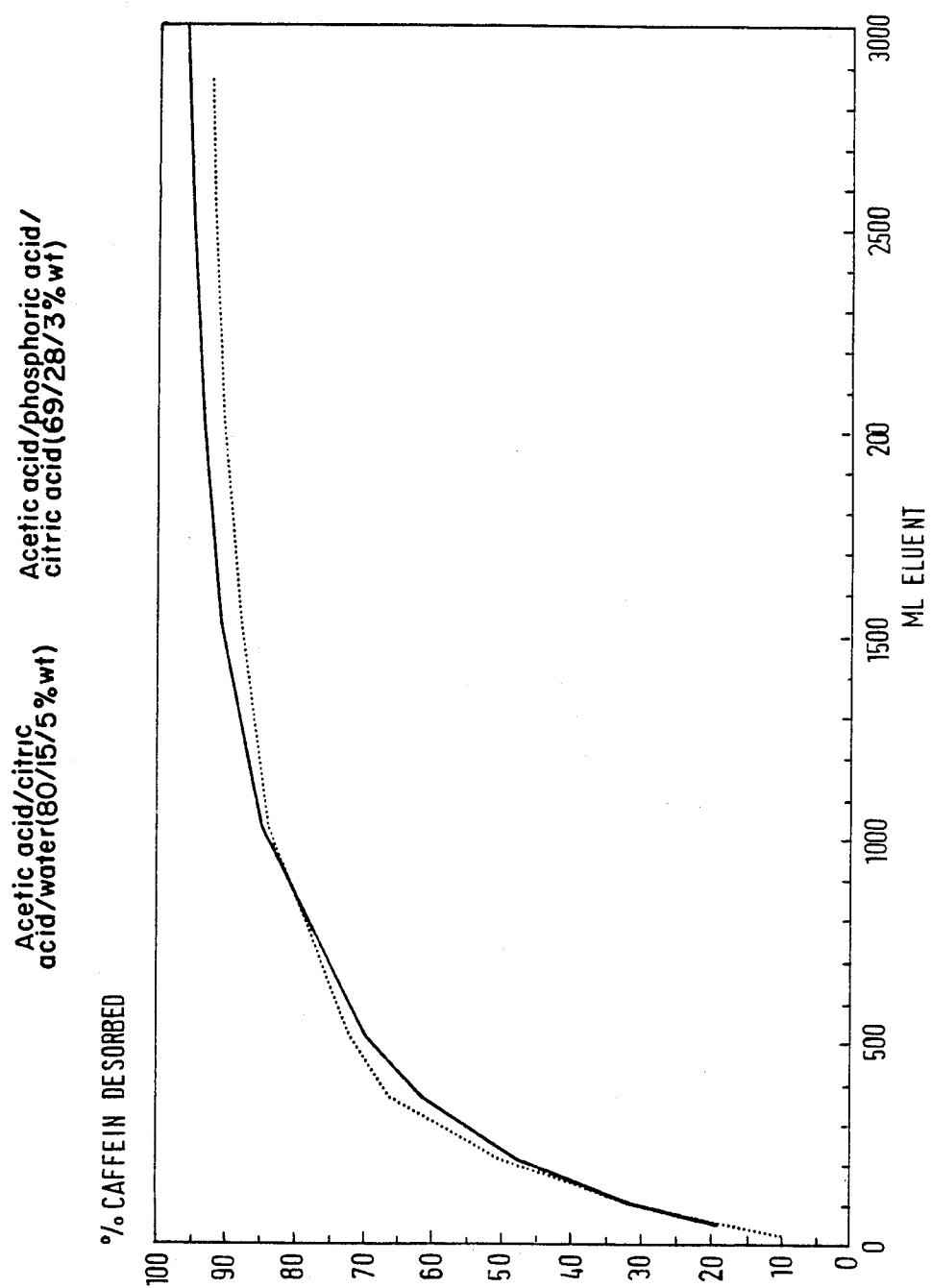

PROCESS FOR RECOVERING CAFFEINE ADSORBED TO ACTIVATED CARBON

This invention relates to a process for recovering caffeine from laden activated carbon by a treatment with an organic acid.

In the literature, much has been published about the recovery of caffeine from activated carbon laden with caffeine, using acid solutions or acids. East German Pat. No. 78,586 relates to the recovery of caffeine from activated carbon laden with caffeine by using more concentrated acids than conventional up to that time, which gave rise to a clearly superior extraction than was accomplished with the weakly acidic solutions up to then used. European patent application no. 42295 relates to the use of glacial acetic acid as an agent for removing caffeine from activated carbon.

European patent application No. 76,620, of the same applicants, indicates that, although glacial acetic acid works best, on the ground of safety considerations it is preferable to sacrifice part of the efficiency and to use less concentrated acetic acid solutions.

European patent application No. 129,609, finally, relates to the use of formic acid or mixtures of formic acid with a slight quantity of water for the recovery of caffeine. According to this last publication, the use of formic acid leads to considerably better extraction results than does the use of acetic acid. Formic acid, however, has a number of disadvantages, including, in particular, its high volatility.

It is an object of the present invention to provide a process for recovering caffeine from laden activated carbon, which process gives a particularly good extraction result, while at the same time no problems arise with regard to the volatility or inflammability of the extraction agent to be used.

These as well as other objects and advantages of he present invention will be better understood by carefully reading the following detailed description of the present invention in conjunction with the accompanying drawing, wherein:

the drawing is a graph showing the results of Example I and Example II wherein the solid line represents the experimental results from Table a (Example I) and the dotted line represents the experimental results from Table b (Example II).

According to the present invention, the process is characterized by treating the activated carbon with a mixture containing at least 65% by weight of acetic acid and at least 2% by weight of citric acid.

We have surprisingly found that when an extraction agent is used, in which at least part of the acetic acid has been replaced by citric acid, on the one hand the advantages of lower inflammability and, on the other hand, particularly good extraction efficiencies are obtained.

Preferred mixtures contain between 65 and 90% by weight of acetic acid.

The proportion of citric acid ranges between 2 and 35% by weight. It is not necessary for the mixture to consist of these two components only. In fact, a portion of the acetic acid may be replaced by other components, but in principle, at least 65% by weight of acetic acid should be contained in the mixture.

Suitable compounds for use in the mixture are, for example, water, phosphoric acid, lactic acid, oxalic acid, benzoic acid, formic acid, glycolic acid, or combinations of two or more of these.

Water is preferred, both from economic considerations and from considerations of extraction efficiency.

Particularly suitable compositions comprise 70–90% by weight of acetic acid, 5–28% by weight of citric acid and 0–25% by weight, preferably 2–20% by weight of water.

Such compositions combine a low inflammability with a very good extraction efficiency.

Moreover, such compositions have the advantage of containing only substances that are regarded as safe (Generally Recognised As Safe, GRAS). This means in practice that it is not a drawback for the activated carbon, after the removal of the caffeine, to contain still a slight amount or traces of the extraction agent. In fact, with these substances, thermal regeneration before re-using the carbon for decaffeination is unnecessary.

In another embodiment of the invention, the combination of acetic acid, citric acid and phosphoric acid is used, for example in proportions of 65–75% by weight of acetic acid, 25–35% by weight of phosphoric acid and 2–5% by weight of citric acid. With such a combination, too, good extraction efficiencies are obtained.

The process according to the invention is preferably carried out at a temperature of more than 100° C., as at these temperatures an efficient extraction takes place. The use of superatmospheric pressures, however, is unnecessary, which of course is a clear advantage. The upper limit of the temperature is not critical, but should not be higher than the temperatures at which the various components become too volatile, or decompose. Preferably, the upper limit is no higher than 200° C., in particular 150° C., as no additional advantages can be achieved above the latter temperature.

The most suitable extraction periods and extraction quantities can be determined by those skilled in the art by means of routine experimentation. Owing to the extremely efficient extraction, the quantity of extraction fluid per quantity of activated carbon may be relatively small. Generally speaking, a 5-fold to 10-fold quantity, by volume, of extracting agent, relative to the quantity of laden activated carbon, is sufficient. These proportions are considerably lower than those required in the prior art, where at least 10–20-fold quantities are required. Naturally, larger quantities may be used according to the invention, but this is not necessary. The carbon laden with caffeine will generally be the product of processes for the removal of caffeine from green coffee. Examples of such processes are described in European patent applications Nos. 40,712, 111,375 and 8398.

After the removal of the caffeine from the carbon, it can be removed from the solution in known manner, for example, by crystallization.

After being substantially fully freed from caffeine, the carbon can be re-used for the absorption of caffeine after the removal of the solvent and/or regeneration.

The invention is illustrated in and by, but not limited to, the following examples.

EXAMPLES I AND II

A commercial activated carbon laden with caffeine and other coffee solids (81.6 g carbon, 3.59 g caffeine) was desorbed with a mixture consisting of 80% by weight of acetic acid, 15% by weight of citric acid and 5% by weight of water by pumping three liters of this liquid over a carbon column having a temperature of 118° C. (downflow). The eluent was collected in a number of fractions and analyzed for caffeine after being cooled. The results are listed in Table a, which shows that 96.1% of the caffeine was desorbed.

TABLE a

| Range (ml) | volume (ml) | caffeine concentr. (g/l) | caffeine absolute (g) | caffeine cumulat (g) | caffeine desorbed (%) | volume cumulat (ml) |
| --- | --- | --- | --- | --- | --- | --- |
| 0–50 | 50 | 33.71 | 0.6855 | 0.6855 | 19.1 | 50 |
| 50–100 | 50 | 8.65 | 0.4325 | 1.1180 | 31.1 | 100 |
| 100–200 | 100 | 5.77 | 0.5770 | 1.6950 | 47.2 | 200 |
| 200–350 | 150 | 3.25 | 0.4875 | 2.1825 | 60.8 | 350 |
| 350–500 | 150 | 1.96 | 0.2940 | 2.4765 | 69.0 | 500 |
| 500–1000 | 500 | 1.08 | 0.5400 | 3.0165 | 84.0 | 1000 |
| 1000–1500 | 500 | 0.44 | 0.2200 | 3.2365 | 90.1 | 1500 |
| 1500–2000 | 500 | 0.199 | 0.0995 | 3.3360 | 92.9 | 2000 |
| 2000–2500 | 500 | 0.133 | 0.0665 | 3.4025 | 94.8 | 2500 |
| 2500–2980 | 480 | 0.102 | 0.0490 | 3.4515 | 96.1 | 2980 |

Similarly, desorption was carried out using a mixture consisting of 69% by weight of acetic acid, 28% by weight of phosphoric acid and 3% by weight of citric acid.

The results are set forth in the following Table b. This shows that 92.3% of the caffeine was desorbed.

The results of the tables are plotted graphically in the accompanying graph. The solid line on the graph represents the experimental results from Table a and the dotted line represents the experimental results from Table b.

TABLE b

| Range (ml) | volume (ml) | caffeine concentr. (g/l) | caffeine absolute (g) | caffeine cumulat (g) | caffeine desorbed (%) | volume cumulat (ml) |
| --- | --- | --- | --- | --- | --- | --- |
| 0–25 | 25 | 14.17 | 0.3543 | 0.3543 | 9.9 | 25 |
| 25–50 | 25 | 10.78 | 0.2695 | 0.6238 | 17.4 | 50 |
| 50–100 | 50 | 10.06 | 0.5030 | 1.1268 | 31.4 | 100 |
| 100–200 | 100 | 6.57 | 0.6570 | 1.7838 | 49.7 | 200 |
| 200–350 | 150 | 3.76 | 0.5640 | 2.3478 | 65.4 | 350 |
| 350–500 | 150 | 1.41 | 0.2115 | 2.5593 | 71.3 | 500 |
| 500–1000 | 500 | 0.85 | 0.4250 | 2.9843 | 83.1 | 1000 |
| 1000–1500 | 500 | 0.29 | 0.1450 | 3.1293 | 87.2 | 1500 |
| 1500–2000 | 500 | 0.204 | 0.1020 | 3.2313 | 90.0 | 2000 |
| 2000–2500 | 500 | 0.113 | 0.0565 | 3.2878 | 91.6 | 2500 |
| 2500–2840 | 340 | 0.074 | 0.0252 | 3.3130 | 92.3 | 2840 |

EXAMPLE III

In the same way as described in Example I, the caffeine-laden carbon was desorbed using a mixture consisting of 95% by weight of acetic acid and 5% by weight of citric acid. After passing 3 l of this mixture over 61.6 g carbon, 93.4% of the caffeine had been removed. The course of the desorption as a function of the quantity of liquid is illustrated in Table c.

TABLE c

| Range (ml) | volume (ml) | caffeine conc. (g/l) | caffeine (g) |
| --- | --- | --- | --- |
| 0–25 | 25 | 5.92 | 0.148 |
| 25–50 | 25 | 8.26 | 0.207 |
| 75–100 | 25 | 5.22 | 0.131 |
| 225–250 | 25 | 4.44 | 0.111 |
| 475–500 | 25 | 2.70 | 0.068 |
| 975–1000 | 25 | 0.60 | 0.015 |
| 1475–1500 | 25 | 0.33 | 0.008 |
| 1975–2000 | 25 | 0.20 | 0.005 |
| 2975–3000 | 25 | 0.068 | 0.002 |

TABLE c-continued

| Range (ml) | volume (ml) | caffeine conc. (g/l) | caffeine (g) |
| --- | --- | --- | --- |
| Coll. fractions: | 2750 | 0.067 | 2.659 |
| Total caffeine: | | | 3.354 |

I claim:

1. A process for recovering caffeine from laden activated carbon by treating the laden activated carbon with an organic acid wherein said activated carbon is treated with a mixture comprising at least 65% by weight of acetic acid and at least 2% by weight of citric acid.

2. A process is claimed in claim 1, wherein said activated carbon is treated at a temperature of more than 100° C.

3. A process as claimed in claim 1, wherein said caffeine is removed from the resulting solution by crystallization.

4. A process as claimed in claim 1, wherein said mixture contains 65–90% by weight of acetic acid.

5. A process as claimed in claim 1, wherein said mixture further contains at least one component selected from the group consisting of water, phosphoric acid, lactic acid, oxalic acid, benzoic acid, formic acid and glycolic acid.

6. A process as claimed in claim 5, wherein said mixture comprises 70–98% by weight of acetic acid, 2–30% by weight of citric acid and 0–25% of weight of water.

7. A process as claimed in claim 6, wherein 2–20% by weight of water is employed in the mixture.

8. A process for decaffeinating coffee by means of activated carbon, followed by recovering the caffeine from the carbon, wherein the caffeine is recovered by using the process as claimed in claim 1.

* * * * *